US008007486B2

(12) United States Patent
Capitaine et al.

(10) Patent No.: US 8,007,486 B2
(45) Date of Patent: Aug. 30, 2011

(54) METHOD AND SET FOR TRANSFERRING A FLUID BETWEEN TWO CONTAINERS

(75) Inventors: Francois Capitaine, Anglet (FR); Olivier Buchs, Capbreton (FR)

(73) Assignee: Technoflex, Bidart (FR)

( * ) Notice: Subject to any disclaimer, the term of this patent is extended or adjusted under 35 U.S.C. 154(b) by 1095 days.

(21) Appl. No.: 11/723,264

(22) Filed: Mar. 19, 2007

(65) Prior Publication Data

US 2008/0177244 A1 Jul. 24, 2008

(30) Foreign Application Priority Data

Jan. 24, 2007 (FR) ..................................... 07 52870

(51) Int. Cl.
*A61M 5/32* (2006.01)

(52) U.S. Cl. ....................................... 604/414; 604/411

(58) Field of Classification Search .................... 604/88, 604/403, 404, 408–416, 905, 44
See application file for complete search history.

(56) References Cited

U.S. PATENT DOCUMENTS

| | | | | |
|---|---|---|---|---|
| 5,364,369 | A * | 11/1994 | Reynolds | 604/187 |
| 6,113,583 | A * | 9/2000 | Fowles et al. | 604/403 |
| 6,269,346 | B1 * | 7/2001 | Cristofich et al. | 705/36 R |
| 6,567,790 | B1 | 5/2003 | Slane | |
| 6,610,040 | B1 * | 8/2003 | Fowles et al. | 604/413 |
| 7,523,918 | B2 * | 4/2009 | Matkovich et al. | 251/149.1 |
| 2003/0107628 | A1 | 6/2003 | Fowles et al. | |

FOREIGN PATENT DOCUMENTS

WO WO 03/082398 10/2003

OTHER PUBLICATIONS

Menachem Brenner, Rangarajan K. Sundaram and David Yermack, Altering the terms of executive stock options, 2000, Journal of Financial and Economics, 57, pp. 103-128.*

Merrill Lynch & Co., Mandalay Resort Group, Floating Rate Convertible Senior Debentures due 2033; Offering Memorandum; Mar. 17, 2003.

Industry Issues Archive; SEC Adopts Proposals Regarding Exchanges and Alternative Trading Systems; http: //www.ici.org/issues/mrkt/arc-ser/98_sec_ats_adopt.http; Dec. 28, 1998.

(Continued)

*Primary Examiner* — Leslie R Deak
*Assistant Examiner* — Philip R Wiest
(74) *Attorney, Agent, or Firm* — Young & Thompson

(57) ABSTRACT

A method and a set for transferring fluid between a first container a second container. The first container is connected to an end of a first transfer body, a first sealing member preventing the fluid communication between these two elements. The second container is closed by a second sealing member. The second container is assembled with a fastening member provided at an end of a second transfer body which is in an inactivated position of the transfer set wherein at least a part of this body is partially inserted within the other end of the first transfer body. Each transfer body has one central passage coaxial to accommodate at least one end of a mobile piercing member. The part of the second transfer body moves along an axis from the inactivated position to an activated position of the transfer set wherein the fluid communication between these two containers is established.

13 Claims, 5 Drawing Sheets

OTHER PUBLICATIONS

Cowan, Arnold, R., Nayar, Nandkumar, Singh, Ajai K.; How high are investment banking fees? The case of standby underwritten convertible calls; Oct. 1999; http;//www.bus.iastate.edu/arnie.

Affiliated Managers Group, Inc.; $200,000,000 Floating Rate High premium and Warrant Convertible Securities due 2033; Offering Memorandum; LIBC Feb. 2003.

Merrill Lynch & Co.; $250,000,000 Affiliated Managers Group, Inc. Floating Rate Convertible Senior Debentures due 2033; Offering Memorandum; Feb. 19, 2003.

Hoadley. Peter; Options Strategy Analysis Tools; http://www.hoadley.net/options/bs.htm.

DerivativesStrategy; Delta Hedging Problems and Solutions; http.//www.derivativesstrategy.com/magazine/archive/1998/0398coll.asp.

Hauser, James L., Journal of Compensation and Benefits; The Stock Option Repricing Dilemma; Nov./Dec. 2001.

Applications of random walkers to Stock Pricing, www. math.mit.edu/stocker/18354.d/financial.pclf; Spring 2004.

* cited by examiner

METHOD AND SET FOR TRANSFERRING A FLUID BETWEEN TWO CONTAINERS

The present invention relates to a method for transferring a fluid between a first container, containing said fluid to be transferred, and a second container. It also relates to a transfer set for carrying out this method for transferring a fluid.

The invention is especially applicable to the transfer of a volume of fluid, contained into a flexible bag, into a vial.

It is known to package a drug under a freeze-dried form into a vial made of glass and to reconstitute this drug before administration to a patient by introduction of a liquid. This liquid is typically contained into a bag or vial for aqueous solution.

This regeneration is carried out by a medical operator and can be made according to two operating modes.

According to a first operating mode, the operator introduce a liquid into the vial containing the drug to be reconstituted using a syringe in order to dissolve its contents. The medicinal solution thus reconstituted is then drawn using the syringe in view of its injection into a flexible bag for aqueous solution. This injection is made through an injection site, i.e., a membrane closing one of the inlet ports of the bag, such as a tubular coupling part, and having the particularity to remain tight after its piercing by a needle.

The second operating mode implements a transfer set, i.e., a tubing especially dedicated to the connection of a bag and a vial in view to the reconstitution of a drug.

This transfer set comprises especially a connector at one of its ends, intended to fix itself to the vial containing the active principle.

This connector comprises a skirt allowing its fitting on the throat of a vial by engaging, the skirt enclosing then at least a portion thereof.

However, this connector of the prior art includes a piercing member such as a beveled needle projecting into the receiving volume of the vial, defined by the skirt. Therefore, this piercing member is going to pierce the closure of the vial during the coupling of the skirt and the vial.

The fluid communication thus established between the connector and the vial define a time interval during which the drug must be used.

Indeed, it is known that to pierce the closure of a vial containing an active principle generates a light sucking in of the vial surrounding air through the connector. This sucked-in air can be at the origin of a contamination of the vial contents.

Thus, it is not possible for the nursing personnel to assemble in advance a set of vials with such connectors in order to administrate drugs to patients.

Moreover, the two operating modes above described require the use of metallic needles that can be dangerous for the nursing personnel.

Still known is a method for reconstituting a drug contained into a vial using a transfer set and a flexible bag containing a liquid, this transfer set having a moving part and a fixed part.

This method of reconstitution requires to connect an end of the transfer set comprising a fixed piercing member to a flexible bag containing a solution to be diluted, to pierce, using a first end of the piercing member, the injection site of said bag, then to fit the other end of the transfer set to a vial. At this stage, the closure of the vial is not yet pierced because the piercing member in fluid communication with the flexible bag by said first end has its other end provided into a passage of the moving part and away relative to the receiving volume of the vial defined by the skirt of the connector. The piercing member being fixed into the set, the operator must then make this moving part to slide into the fixed part in order to bring the closure in contact with the end of the piercing member and to establish a fluid communication between the bag and the vial.

It clearly appears that the establishment of a fluid communication between the bag and the vial is a long process requiring, moreover, a skilled nursing personnel.

Moreover, handling errors are possible with the inherent risk of a contamination of the reconstituted drug by introduction of surrounding air because the transfer set does not have any safety member.

In addition, the liquid comes initially into contact with the internal walls of the transfer set before the fluid communication be established between the set and the vial. The liquid may again be exposed to a contamination resulting, for example, from an intake of external air into the transfer set.

Lastly, there is not any indication external to the transfer set allowing the operator to monitor, before use and with a simple glance, the activated or not state of the set in order to check if the sterility of the implemented unit is still whole.

There is thus a pressing need for a transfer set allowing to establish a fluid communication between a bag and a vial for aqueous solution without breaking the asepsis of the containers.

This transfer must be carried out without risk for the nursing personnel.

It is significant that the nursing personnel has less operations to carry out in order to reconstitute a drug. These gestures must be simple in order to decrease the risks of handling error.

Finally, the nursing personnel must be able to monitor each step of the process for reconstituting a drug.

The object of the present invention is thus to propose a method and an element for transferring a fluid between a first container containing said fluid and a second container containing the drug to be reconstituted which have simple design and operating mode, and allow to ensure a total asepsis during the fluid transfer between the two containers.

To this end, the invention relates to a method for transferring a fluid between a first container containing a fluid and a second container, the first container being connected to a first end of a first transfer body, a first sealing member preventing the fluid communication between the first container and the first transfer body, the second container being closed by a second sealing member.

According to the invention, this method includes the following successive steps:

a) of assembling the second container with a fastening member provided at a first end of a second transfer body, the second transfer body being into an inactivated position of the transfer set wherein at least a part of the second transfer body is partially inserted within the second end of the first transfer body, each transfer body further comprising a central passage to accommodate at least one of the ends of a mobile piercing member, these passages being coaxial, the central passage of the second transfer body opening into the fastening member in order to allow the end of the piercing member to pass towards the second sealing member, the end of this second sealing member being provided away so that the sealing members are non-bored after this assembly, b) said part of the second transfer body being movable along a moving axis from the inactivated position to an activated position of the transfer set wherein the fluid communication between the first container and the second container is established, of moving this part along the moving axis up to the activated position of the transfer set, the only displacement of this part involving first the piercing of the second sealing member and then the piercing of the first sealing member by the mobile piercing member comprising a boring element on each of its ends, c) of introducing at least part of the fluid of the first container into said second container in order to mix it the contents of the second container.

This method advantageously enables a timing of the transfer, i.e., the carrying of a succession of simple steps according to a given order leading to the establishment of a fluid communication between two containers.

The only displacement by the operator of part of the second transfer body from an inactivated position to an activated position of the transfer set involves a movement of the mobile piercing member which first pierces the sealing member of the second container, and then the sealing member of the first container containing the fluid. Thus by a simple action, for example, a sliding motion or a rotation driving of the part of the second transfer body by the operator, a direct fluid communication is established between the first container and the second container by means of the piercing member.

This method for transferring provides thus an increased safety because it is impossible, on one hand, to make a wrong manipulation and, on the other hand, the asepsis of the containers is preserved by the piercing, in a first time, of the second container followed then by the piercing of the first container containing the fluid, the set comprising a set of sealing members.

For this reason, the transfer set of the invention can comprise sealing members provided on both sides of the piercing member in a unused state in order to ensure the tightness of the piercing member itself.

In a purely illustratively way, the first container being a flexible bag for aqueous solution and the second container being a vial containing an active principle under the form of a powder, during step c), the operator places the vial under the flexible bag and applies short and low pressures on this one in order to send liquid into the vial. The operator must then agitate the vial to ensure a complete reconstitution of the drug. Finally, it reverses the unit in order to place the vial above the bag and presses in a fast and repeated way on the bag to send air into the vial and to drive out the liquid from it. This process is repeated three times in order to make sure that there does not remain any powder in the vial. The flexible bag contains then a dose of drug and is ready to be connected to a patient for a perfusion.

In various particular embodiments of this method for transferring fluid, each having its particular advantages and being liable to form many possible technical combinations:

- one of the transfer bodies comprising at least a removable clamping member to hold the movable part along the moving axis in its inactivated position, this clamping member is removed before step b), This clamping member is, for example, a ring connected to the second end of the first transfer body, this ring cooperating with a stop provided on the external surface of the second transfer body to prevent the movement of the movable part of the second transfer body.

This clamping member makes it advantageously possible to the operator to monitor, before use, the activated or not state of the transfer set in order to check if the sterility of the unit implemented is still complete.

- The first transfer body and the movable part comprise non-return means cooperating to prevent the first and second transfer bodies to be dissociated,
- at step b), the part of the second transfer body is moved in translation along the moving axis or in rotation around this moving axis, this translation or rotation leading via driving means cooperating with the mobile piercing member to a rotation thereof,
- the driving means first drive the mobile piercing member for rotation around its main axis and then for translation along the moving axis,
- the driving means drive the mobile piercing member for rotation around its main axis and for translation along the moving axis,
- the first end of the first transfer body being constituted by the central passage into which is provided the first sealing member and the first container comprising an inlet port, this central passage and the inlet port are beforehand assembled in step a),
- the first end of the first transfer body being constituted by the central passage into which is provided the first sealing member and the first container being a flexible bag, the central passage is interdependent with the flexible bag and form an inlet port thereof.

In an illustratively way, the flexible bag comprises two walls intended to define the inside volume of this bag, said walls being unified together by welding, for example, the first end of the first transfer body is provided between these two walls at the lower end of the bag. The central passage of the first transfer body establishes a fluid communication between the inside volume of the bag and the inside of the transfer set. However, the first sealing member provided in the central passage at the end of the first transfer body forms a tight barrier into the inactivated position of the transfer set,

- the portion of the first central passage provided at the first end of the first transfer body and the boring element accommodated into the first passage are intended to cooperate in order to guide the fluid of the first container in the internal channel of the piercing member, In an illustratively way, the first central passage having a conical portion provided at the first end of the first transfer body, the boring element accommodated into the first passage comprises a conical portion at the end of which is provided a beveled edge.

- The first sealing member being provided in the central passage of the first transfer body and the central passage of the second transfer body comprising a divisible membrane at its end so as to guarantee the sterility of the piercing member, during step b) this membrane is pierced before to pierce the second sealing member, This embodiment enables to guarantee the asepsis of the piercing member before use of the transfer set.

- In step a), the second container and the fastening member are assembled in a tight way by means of a lip provided at the end of the central passage of the second transfer body, this lip being provided in tight contact with the second sealing member after assembly of the fastening member and the second container.

The invention also relates to a transfer set for carrying out the method for transferring a fluid as previously described. According to the invention, this transfer set comprises:

- a first transfer body comprising a first end and a second end, the first end being intended to be connected to a first container, the first transfer body comprising a first central passage accommodating at least a first end of a mobile piercing member, this first end comprising a boring element, a first sealing member being intended to prevent the fluid communication between the first container and the first transfer body, the first end being intended to be accommodated into the central passage away from this sealing member so that the first sealing member is non-bored into an inactivated position of the transfer set, a second transfer body comprising a first end and a second end, the first end having a fastening member to receive and fix a second container, the second container being closed by a second sealing member, the second transfer body comprising a second central passage accommodating at least the second end of the mobile piercing member, this end comprising a boring element, the first and second central passages being coaxial, the second central passage opening into the fastening member to allow the second end to pass towards the second sealing member, the second end being intended to be provided into the second passage apart from the second sealing member so that the second sealing member is non-bored into an inactivated position of the transfer set, at least part of the second transfer body being movable along a moving axis from an inactivated position of the transfer set wherein this part of the second transfer body is partially inserted within the second end of the first transfer body to an activated position of the transfer set wherein a fluid communication between the first and second containers is established, driving means cooperating with the mobile piercing member to move this piercing member along the moving axis during the movement of said part from the inactivated position to the activated position, the piercing member being intended to first bore the sealing member closing the second container and then the sealing member of the first container during its displacement.

In a purely illustratively way, the first container can be a flexible bag or a vial and the second container, a drug vial.

In various particular embodiments of this transfer set, each having its particular advantages and being liable to form many possible technical combinations:

one of these transfer bodies includes at least a removable clamping member to hold said part into the inactivated position of the transfer set, the driving means are selected into the group comprising at least a rotation guiding rail in order to receive one or more guiding elements provided projecting on the piercing member, at least a translation guiding rail in order to receive one or more guiding elements provided projecting on said piercing member, a means to drive said mobile piercing member during the movement of said movable part or yet, combinations of these elements, the rotation guiding rail being an helical groove provided on the internal surface of one of said central passages, the guiding elements are lugs, the second transfer body includes, on its external surface, non-return notches intended to cooperate with holes provided on the wall of the first transfer body for the translation of the movable part along said moving axis, the piercing member comprising projecting guiding elements, this piercing member is provided in the central passages so that the guiding elements abut against a portion of one of the transfer bodies, this portion being non-continuous so that a rotation of the piercing member around its axis makes it possible to release the piercing member to allow its movement along the moving axis.

The piercing member can possibly comprise one or more frangible links interdependent with at least one of the transfer bodies to hold the mobile piercing member so placed, into the inactivated position of the transfer set.

the central passage of the first transfer body further includes one or more elastically retractable projections provided within the central passage to block the end of the piercing member during the movement of the movable part along the moving axis. These elastically retractable projections are intended to allow the end of the piercing member to pass, for its displacement along the moving axis, after piercing of the sealing member of the second container. Thus, and only in a purely illustratively way, the required effort to bore the closure of a vial containing a drug to be reconstituted is sufficient for the piercing member to retract these projections.

The invention will be described more in detail with reference to the annexed drawings in which:

FIG. 1 schematically represents a transfer set in a first embodiment of the invention, this transfer set being into an inactivated position;

Figure 5A:
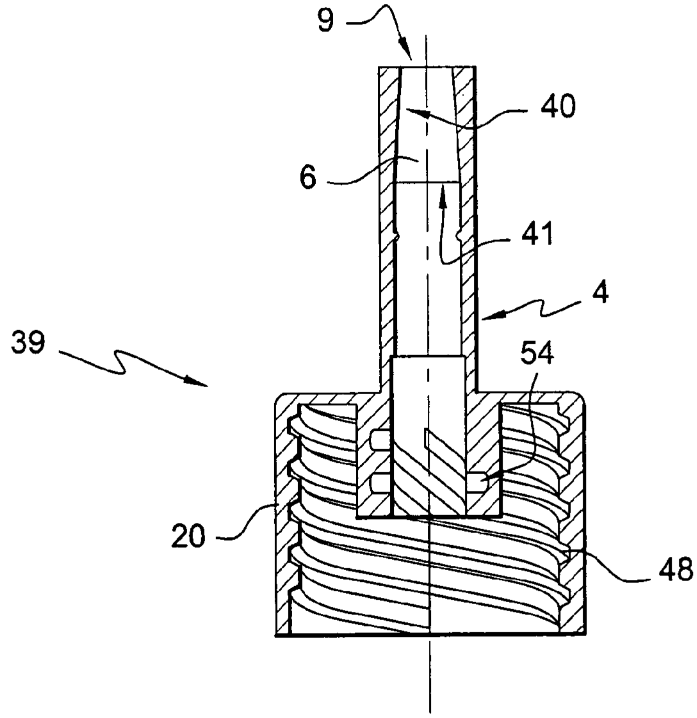
Figure 5B:
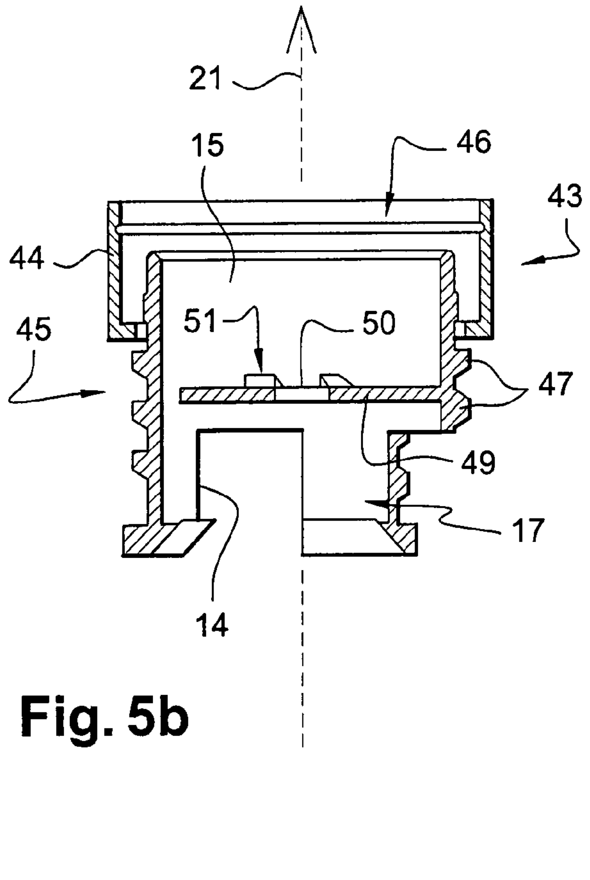
Figure 5C:
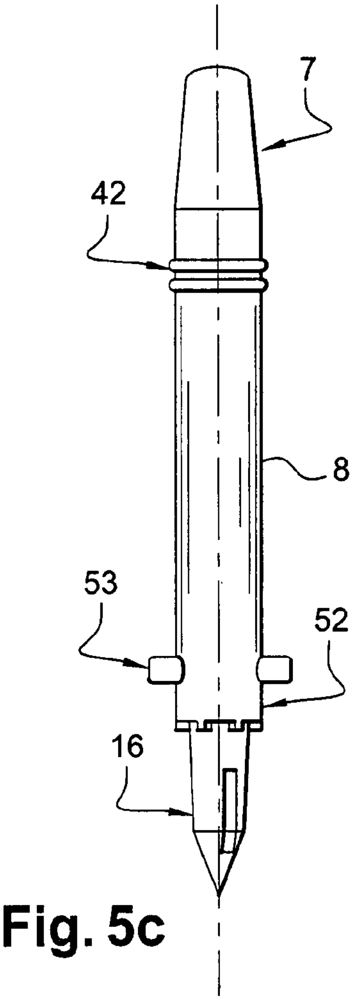

FIG. 5 schematically represents a transfer set in a second embodiment of the invention, the cross-section views show the first transfer body (FIG. 5*a*), the second transfer body (FIG. 5*b*) and the piercing member (FIG. 5*c*).

Figure 1:
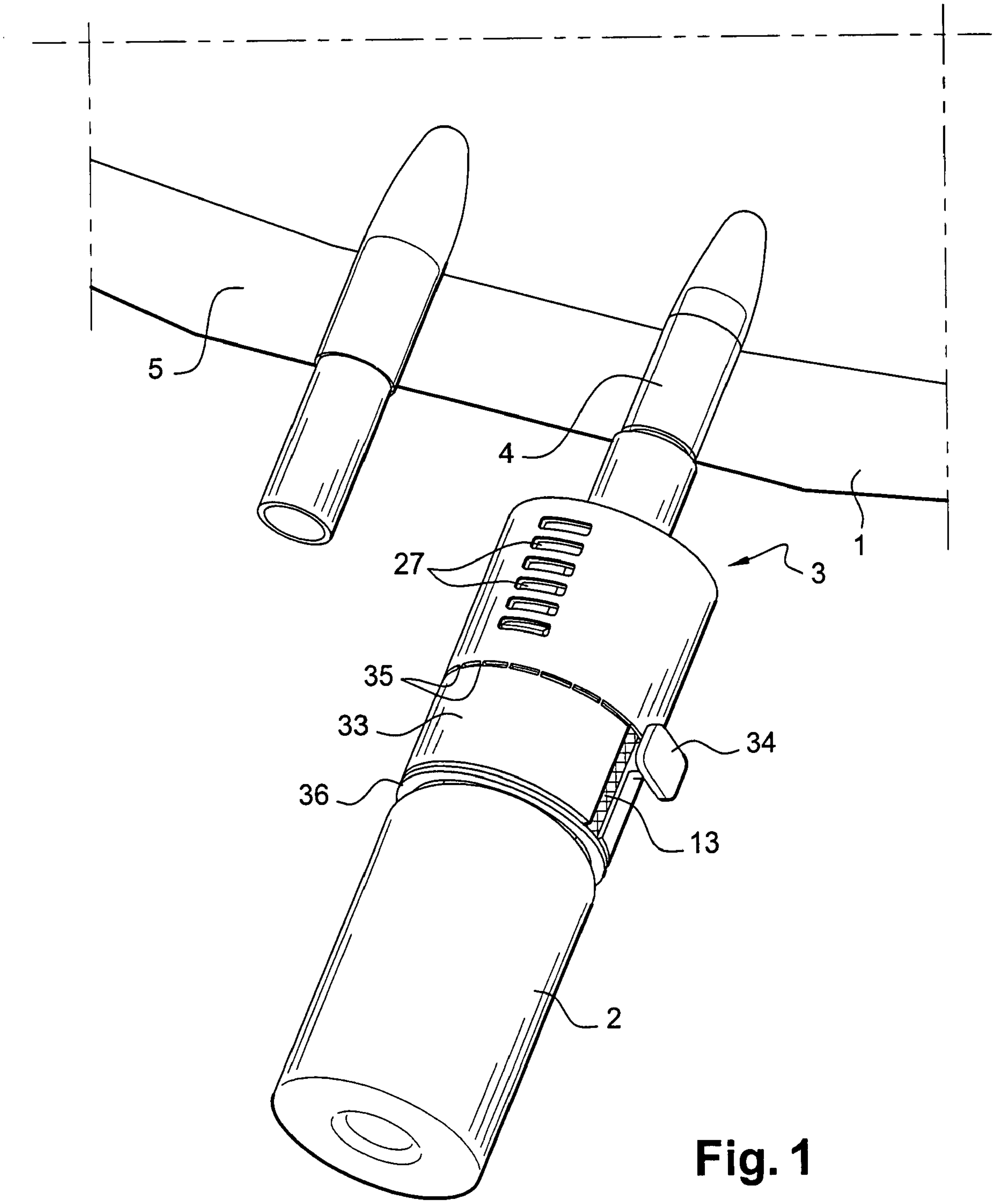
Figure 2:
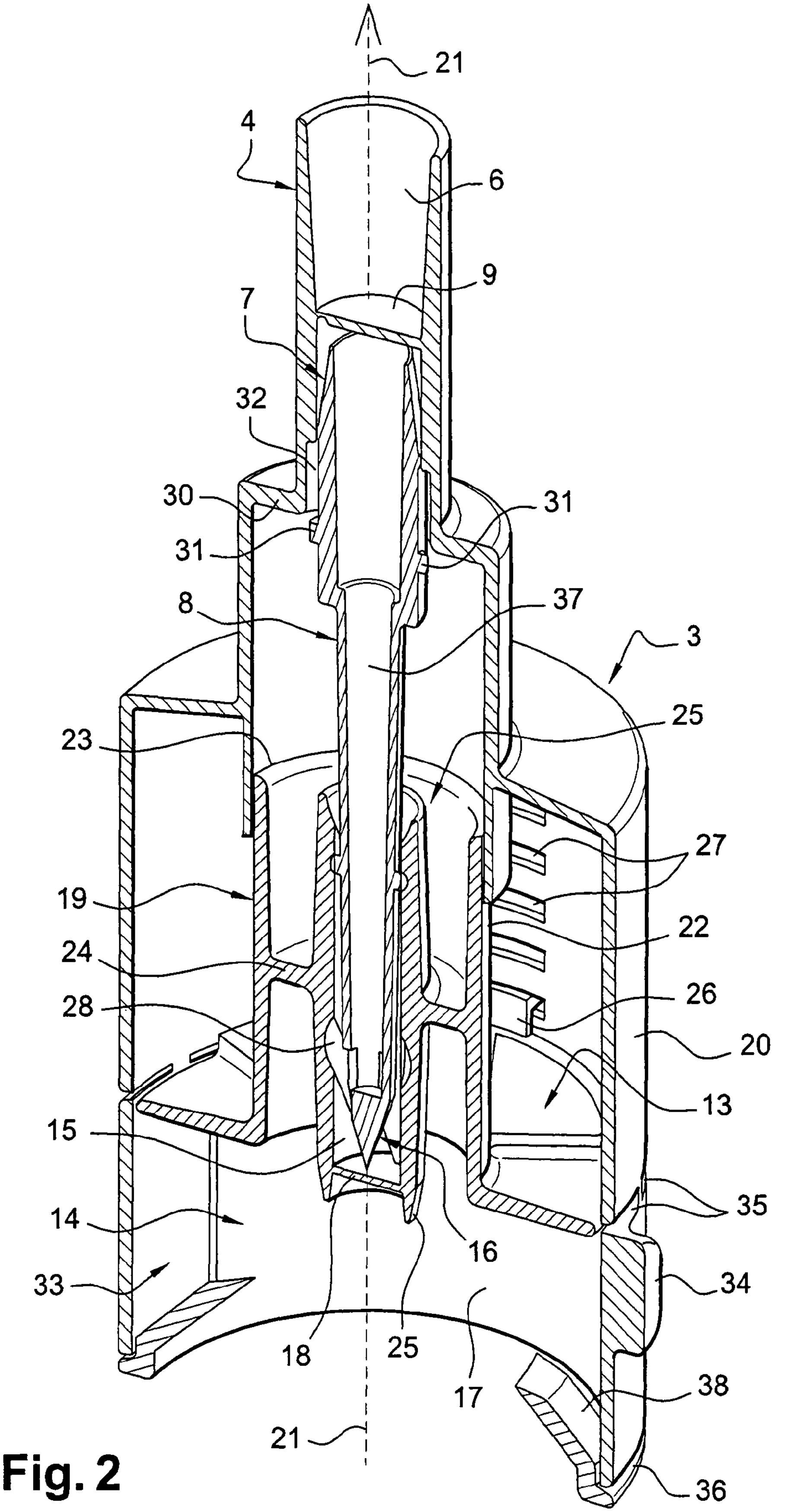
FIG. 2 is a cross-section of the transfer set of FIG. 1 showing the first and second transfer bodies and the mobile piercing member.
Figure 3:
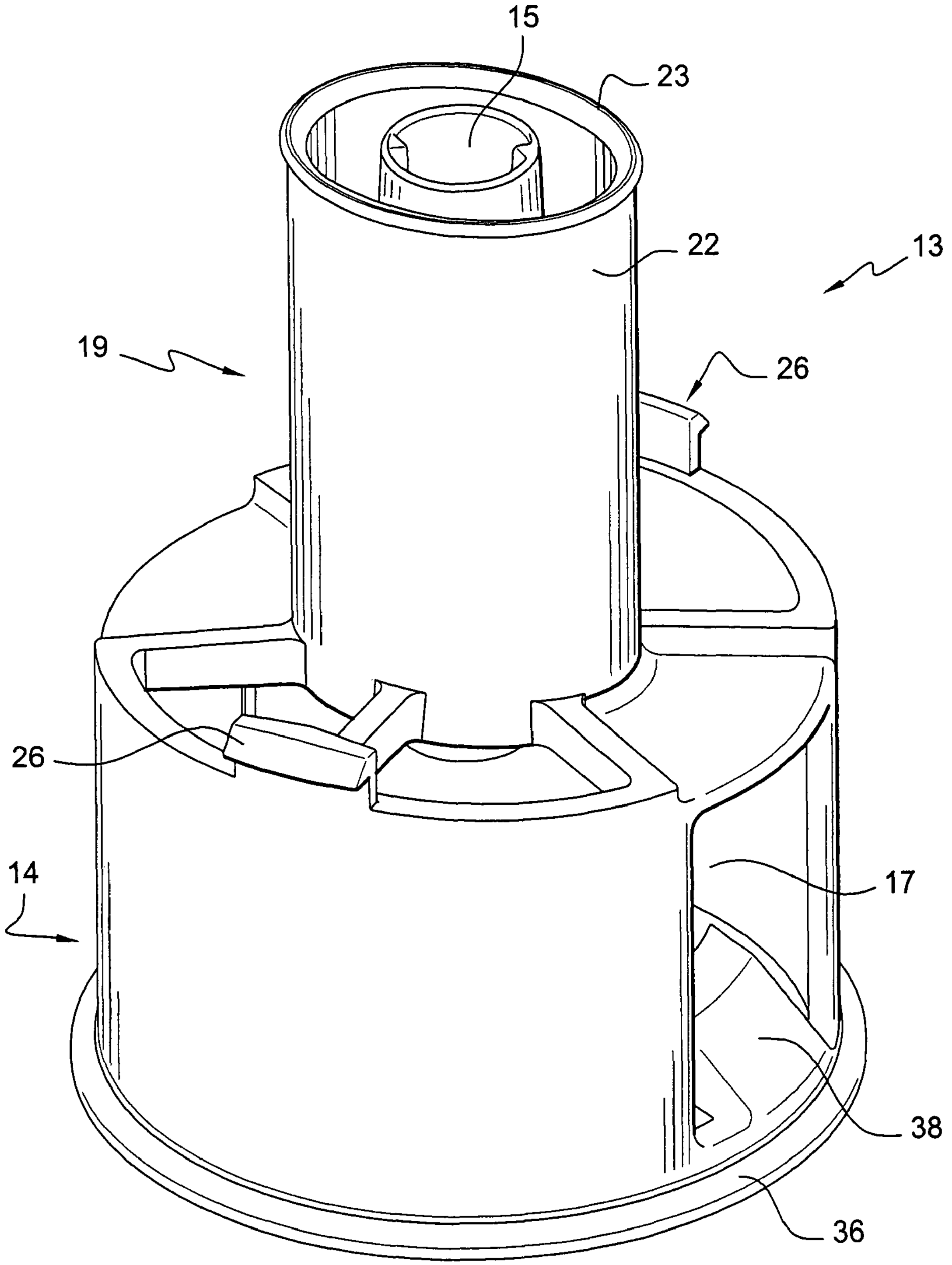
FIG. 3 is a perspective view of the second transfer body of the set of FIG. 1.
Figure 4:
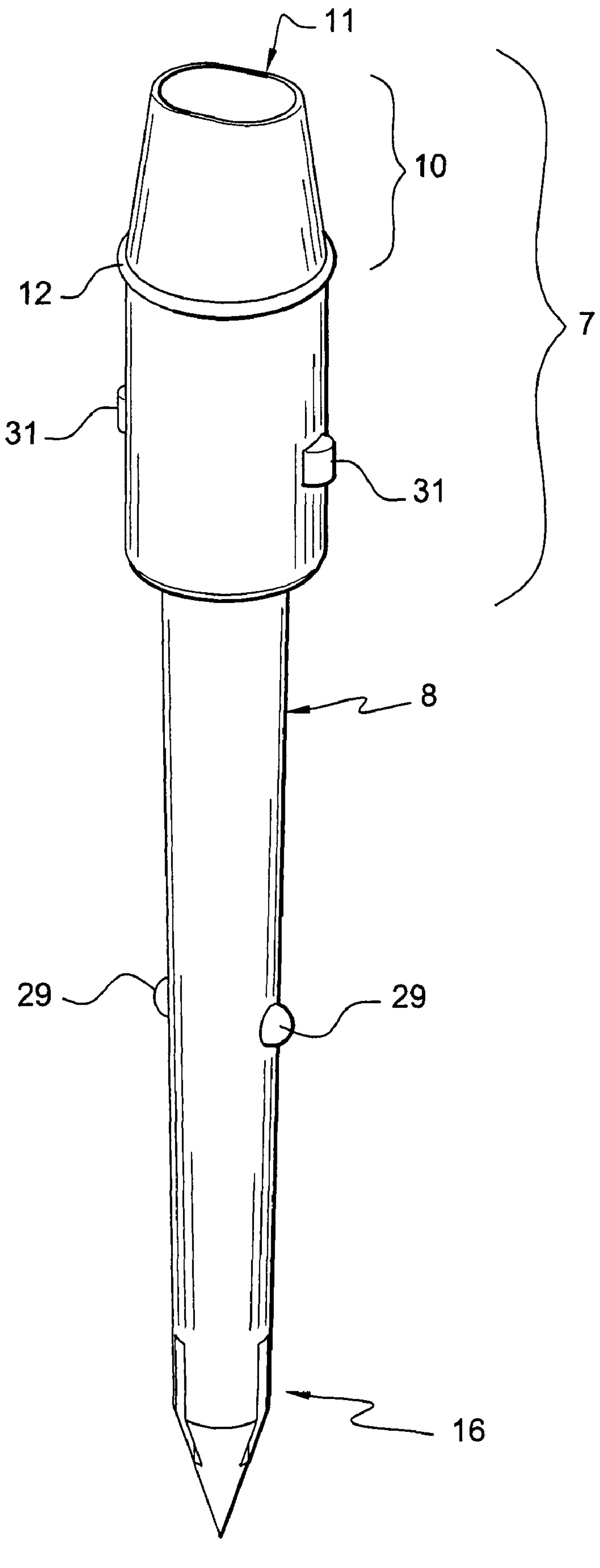
FIG. 4 is a perspective view of the piercing member of the transfer set of FIG. 1.

FIGS. 1 and 2 show a transfer set into a first embodiment of the invention. The transfer set is shown on FIG. 1 into an inactivated position. A first end of this set is connected to a first container 1, such as a flexible bag for aqueous solution while the other end of this transfer set is connected to a drug vial 2 containing a drug to be reconstituted.

The transfer set comprises a first transfer body 3 comprising a first end 4 and a second end. First end 4 is provided between two walls 5 of the bag 1 defining the inside volume thereof and is interdependent with these walls 5. This first end 4 thus forms an inlet port of the bag 1 which is provided at the lower end of the latter.

The first transfer body 3 comprises a first central passage 6 accommodating a first end 7 and part of the body of a mobile piercing member 8.

This first end 7 of the piercing member is provided apart into the first passage 6 relative to a first sealing member 9, which makes it possible to prevent the fluid communication between first container 1 and the first transfer body 3. This sealing member 9 is here a frangible membrane. Preferably, the membrane 9 includes one or more predetermined weakening zones so as to facilitate its breakage, or even, to cause the breakage thereof in a predetermined number of pieces, these pieces remaining attached to the wall of the central passage of the first transfer body. For that, the membrane can also include a reinforcement area on its periphery ensuring its union with said passage.

The first end 7 of the piercing member comprises a generally cylindrical and hollow portion having a diameter more significant than the remainder of the body of piercing member 8. This portion terminates at its end by a conical part 10 to ensure the tightness of the membrane/piercing member connection after breakage thereof. The end of this conical part 10 has a bevel 11 to facilitate the cutting of the first sealing member 9.

The first end 7 includes also a seal 12. This seal 12 is, for example, a continuous pad which allow, from its setting in contact with the internal wall of the central passage 6, to form a tight connection between this passage 6 and the end of piercing member 8.

This first end 7 thus makes it possible, after breakage of the first sealing member 9, to guide the fluid mainly into the internal channel 37 of the piercing member 8 so as to forward it directly to the other end of the piercing member and thus into the second container 2.

The set also includes a second transfer body 13 comprising a first end and a second end, said first end having a fastening member 14 in order to receive and fix the top of a second container 2. This fastening member 14 comprises here a skirt allowing to receive and fix snappily the throat of a vial, the skirt enclosing then a portion of this vial 2. The skirt includes projections 38 to engage snappily the top of vial 2. The vial 2 is closed by a second sealing member of the closure to be pierced type (not shown). But it could also be a frangible membrane or a different one.

The second transfer body 13 comprises a second central passage 15 accommodating the second end 16 of the mobile piercing member 8. The latter comprises a boring element of tip type. The first and second central passages 6, 15 are coaxial.

The second central passage 15 opens into the receiving volume 17 on top of the vial defined by the skirt of the fastening member 14. While thus opening into this receiving volume 17, this second passage 15 allows the second end 16 of the piercing member to pass towards the second sealing member to pierce it with said end.

Into this inactivated position of the transfer set, the second end 16 of the piercing member is provided within the second central passage 15 apart from the second sealing member so that this one is non-bored. The second end 16 of the piercing member is here provided out of the receiving volume of the fastening member 14 inside the second passage 15 while being separated from this volume by a frangible membrane 18 provided into the second central passage 15. The piercing member 8 is thus surrounded at each of its ends 7, 16 by a sealing member 9, 18 ensuring the asepsis of this piercing member 8.

This frangible membrane 18, as the membrane 9 into the first passage 6, can include one or more predetermined weakening areas so as to facilitate its breakage, as well as a reinforcement area on its periphery in order to ensure the union of the pieces resulting from the breakage of membrane 18 to the second central passage 15.

The second central passage 15 comprises at its end, a lip 25 intended to come into contact with the closure of the vial 2 after connection of the top of vial 2 and the fastening member 14 so as to ensure the tightness of the connection between the vial 2 and the fastening member 14.

The transfer set is made of a plastic material preferably selected into the group comprising the polycarbonate or a derivative thereof, a polyolefin (such as polyethylene, polypropylene, or a polypropylene copolymer) and the polystyrene. It is preferably carried out by molding.

A part 19 of the second transfer body 13 is partially inserted within the second end 20 of the first transfer body 3. This part 19 is movable along a moving axis 21 from the inactivated position of the transfer set presented on FIG. 1 to an activated position wherein a fluid communication is established between the first and second containers 1, 2.

This part 19 comprises an interdependent cylindrical passage 22 of the fastening member 14. At the end of this cylindrical passage 22 is provided a seal 23 ensuring a tight connection between this passage 22 and the first main passage 6 of the first transfer body 3.

The second central passage 15 is connected to this cylindrical passage 22 while being centered on this one. A joining member 24 of the annular disc type connects the second central passage 15 to the cylindrical passage 22. The second central passage 15 comprises advantageously a guiding area 25 of piercing member 8 having here the form of a widened part of the central passage 15.

The first and second transfer bodies 3, 13 comprise non-return means cooperating in order to prevent these transfer bodies from being dissociated. These means are, for example, non-return notches 26, provided on the higher part of the fastening member 14, which are intended to cooperate with regularly spaced holes 27 provided on the wall of the first transfer body 3.

These non-return notches 26 also allow a translation of the movable part 19 of the second transfer body 13. Indeed, by pushing the second transfer body inside the second end of the first transfer body 3, the non-return notches are retracted to pass from hole to hole 27.

The translation of this part 19 leads, via driving means cooperating with the mobile piercing member 8 to a rotation thereof.

These driving means comprise a rotation guiding rail 28 receiving two guiding elements 29 provided as projecting on the body of piercing member 8. The guiding rail 28 for rotation is here an helical groove provided on the internal surface of the second central passage 15 and the projecting guiding elements 29 are pins.

Moreover, the first central passage 6 has a section decrease forming a shoulder 30 of the passage. The first end 7 of the piercing member comprises, on the external surface of its generally cylindrical portion two projections 31 intended to abut against this shoulder 30 from the first passage 6. The piercing member 8 is thus blocked in position along the moving axis 21 in order to initially allow the piercing of the vial 2 closure. By further moving in translation said movable part 19, the piercing member 8 carries out a rotation on itself until the projections 31 are placed facing to translation guiding grooves 32 allowing the translation of the piercing member 8 along the moving axis 21. End 7 of the piercing member can then bore the first sealing member 9 and thus ensure the establishment of a fluid communication between two containers 1, 2.

The first transfer body 3 can still include a removable clamping member to hold the movable part 19 into the inactivated position of the transfer set. This clamping member comprises, for example, a ring 33 comprising a tab 34 making a handle. This ring 33 is connected by frangible links 35 at the second end of the first transfer body 3. This ring 33 cooperates with a stop 36 provided on the external surface of the second transfer body 13 to hold the part 19 into the inactivated position. The operator has only to draw tab 34 to break frangible links 35 and to release the second transfer body 13 in order to carry out the fluid transfer.

FIG. 5 shows the transfer set of another embodiment of the invention. The elements of the FIG. 5 showing the same references as the elements of FIGS. 1 to 4 represent the same objects and thus will not be described again.

This transfer set comprises a first transfer body 39 comprising a first end 4 and a second end 20. The first end 4 is intended to be connected to the inlet port of a first container 1, such as a flexible bag. This first transfer body comprises a first central passage 6 intended to receive a first end 7 and a part of the body of a mobile piercing member 8. The end 7 of the mobile piercing member 8 is conical and beveled. The bevel enables to facilitate the piercing of the first sealing member while the contact cone of the end of the piercing member 8/conical part 40 of the first central passage 6 enables to ensure the tightness of this contact.

The first passage 6 has at the first end 4, a conical part 40 as well as a snap ring 41 enabling a positioning of the piercing member 8. The piercing member 8 has, on its external surface, a groove 42 intended to cooperate with this snap ring 41.

It also comprises a second transfer body 43 comprising a first fixed part 44 connected to a second end 20 of the first transfer body 39 and a second part 45 movable along the moving axis 21, the second part 45 being movable relative to the fixed part 44.

The first fixed part 44 is connected to this second end 20 by joining members such as a snap ring 46 provided on the internal surface of the first fixed part 44, this snap ring 46 cooperating with a groove (not shown) provided on the external surface of the second end 20.

The second part 45 movable along the moving axis 21 and the second end 20 of the first transfer body 39 being cylindrical, the movable part 45 has, on at least a portion of its external surface a threaded hole 47 and the second end 20 of the first transfer body 39 has, on at least a portion of its internal surface, a threading 48 to allow the movement of the part 45 relative to this second end 20 along said moving axis 21.

The transfer set thus differs from that described previously by the fact that the operator moves the movable part 45 of the second transfer body 43 with rotation around the moving axis 21. This rotation leads, via driving means cooperating with the piercing member 8 to a rotation thereof and a translation along the moving axis 21 to allow the piercing of the first sealing member 9 provided at the end of the first central passage 6.

These driving means comprise, on one hand, a means to drive the mobile piercing member 8 when the movable part 45 is moved under the action of the operator. This means comprises a plate 49 provided into the second central passage 15 and comprising a central hole 50 for allowing the boring element 16 of the piercing member to pass. This hole 50 is surrounded by teeth 51 intended to cooperate with teeth 52 provided on the body of the piercing member 8 to connect the piercing member and the movable part 45. Thus, a rotation driving of the movable part 45 involves a rotation of the mobile piercing member 8. The driving means further comprise guiding elements such as pins 53 projecting from the body of the piercing member 8. These pins 53 are intended to cooperate with a rotation guiding rail 54, such as an helical groove provided into the first central passage 6 to ensure the translation of the piercing member 8 along the moving axis 21 by its rotational movement initiated by the means to drive the mobile piercing member 8.

Frangible links (not shown) connect the second end 20 of the first transfer body 39 and the movable part 45 along the moving axis 21 so as to ensure the inviolability of the transfer set as long as they are not broken.

The invention claimed is:

1. A transfer set for transferring a fluid between a first container (1) containing a fluid and a second container (2), said transfer set comprising:

a mobile piercing member (8) with a first end (7) and a second end (16);

a first transfer body (3) comprising a first end (4) and a second end, said first end (4) configured to be connected to said first container (1), said first transfer body (3) further comprising a first central passage (6) accommodating at least the first end (7) of the mobile piercing member (8), said first end (4) of the first transfer body (3)) comprising i) a boring element, and ii) a first sealing member (9), the first sealing member (9) configured to prevent the fluid communication between said first container (1) and said first transfer body (3), said first end (7) of the mobile piercing member configured to be accommodated into said central passage (6) away from said first sealing member (9) so that said first sealing member (9) is non-bored into an inactivated position of said transfer set;

a second transfer body (13) comprising a first end and a second end, said first end of the second transfer body (13) having a fastening member (14) to receive and fix said second container (2), said second container being closed by a second sealing member, said second transfer body (13) further comprising a second central passage (15) accommodating at least the second end of said mobile piercing member (8), said second end (16) of the mobile piercing member comprising a boring element, said first and second central passages (6, 15) being coaxial, the second central passage (15) opening into said fastening member (14) to allow said second end of the mobile piercing member to pass towards the second sealing member, said second end of the mobile piercing member being configured to be provided into said second passage (15) apart from said second sealing member so that said second sealing member is non-bored into an inactivated position of said transfer set, wherein at least a part of said second transfer body (13) is a moveable part movable along a moving axis (21) from an inactivated position of the transfer set wherein said moveable part of said second transfer body (13) is partially inserted within the second end of said first transfer body (3) to an activated position of the transfer set wherein a fluid communication between said first and second containers (1, 2) is established; and driving means cooperating with said mobile piercing member (8) to move said piercing member (8) at least in rotation along said moving axis (21) during the movement of said movable part (19, 45) from the inactivated position to said activated position, wherein displacement of said piercing member (8) first bores the second sealing member closing said second container (2) and then second bores the first sealing member of the first container (1), wherein, said movable part (45) is cylindrical, said second end of the first transfer body (3) is cylindrical, said movable part includes, on at least a portion of its external surface, a threaded hole (47); and said second end of the first transfer body (3) includes, on at least a portion of its internal surface, a threading (48) to allow movement of said movable part (45) relative to said second end of the first transfer body (3) along said moving axis (21), said means to drive said mobile piercing member (8) is a plate (49) provided into the second central passage (15) and comprising a central hole (50) for allowing the boring element of the piercing member (8) to pass, said hole (50) being surrounded with teeth (51) intended to cooperate with teeth (52) provided on the body of the piercing member (8) to connect said piercing member (8) and said movable part.

2. The set according to claim 1, wherein one of said first and second transfer bodies includes at least a removable clamping member to hold said moveable part into said inactivated position.

3. The set according to claim 2, wherein said clamping member comprises a ring (33) including a tab (34) making a handle, said ring (33) being connected by frangible links (35) to said second end of the first transfer body (3), said ring cooperating with a stop (36) provided on the external surface of said second transfer body (13) to hold said movable part (19, 45) into said inactivated position.

4. The set according to claim 2, characterized in that said clamping members are frangible links connecting said second end of the first transfer body (3) and said movable part (19, 45) along said moving axis (21).

5. The set according to claim 1, characterized in that said driving means are selected into the group comprising at least a rotation guiding rail in order to receive one or more guiding elements provided projecting on the piercing member (8), at least a translation guiding rail in order to receive one or more guiding elements provided projecting on said piercing member (8), a means to drive said mobile piercing member (8) during the movement of said movable part or yet, combinations of these elements.

6. The set according to claim 5, characterized in that said rotation guiding rail being an helical groove (28, 54) provided on the internal surface of one of said central passages (6, 15), said guiding elements are lugs (29, 53).

7. The set according to claim 1, wherein, said second transfer body (13) includes i) a first fixed part connected to said second end of said first transfer body (3) by joining members and ii) a second movable part along said moving axis (21), said second movable part being mobile relative to said fixed part.

8. The set according to claim 1, characterized in that said second transfer body (13) includes, on its external surface, non-return notches intended to cooperate with holes provided on the wall of the first transfer body (3) for the translation of said movable part along said moving axis (21).

9. The set according to claim 8, characterized in that the central passage of the first transfer body (3) further includes one or more elastically retractable projections provided within said central passage to block the end of said piercing member (8) during the movement of said movable part along said moving axis (21), said elastically retractable projections being intended to allow said end of the piercing member (8) to pass after piercing of the sealing member of said second container (2).

10. The set according to claim 8, characterized in that, said piercing member (8) comprising projecting guiding elements, said piercing member (8) is provided into said central passages so that said guiding elements abut against a portion of one of the transfer bodies, said portion being non-continuous so that a rotation of said piercing member (8) makes it possible to release said piercing member (8) to allow its movement along said moving axis (21).

11. The set according to claim 8, characterized in that, said piercing member (8) comprising projecting guiding elements, said piercing member (8) is provided into said central passages so that said guiding elements abut against a portion of one of the transfer bodies, said portion being non-continuous so that a rotation of said piercing member (8) makes it possible to release said piercing member (8) to allow its movement along said moving axis (21), said piercing member (8) comprising one or more divisible links interdependent with at least one of the transfer bodies to hold said mobile piercing member (8) so placed, into the inactivated position of the transfer set.

12. The set according to claim 1, characterized in that the portion of the first central passage provided at the first end of the first transfer body (3) and said boring element accommodated into said first passage are intended to cooperate in order to guide the fluid from the first container (1) into the internal channel of the piercing member (8).

13. The set according to claim 1, characterized in that said first and second transfer bodies (13) comprise non-return means cooperating in order to prevent said first and second transfer bodies (3,13) to be dissociated.

* * * * *